United States Patent [19]

Levesque

[11] Patent Number: 5,361,627
[45] Date of Patent: Nov. 8, 1994

[54] METHOD AND APPARATUS FOR THE MEASURING THE CAPILLARY ATTRACTION DEVELOPED AT A SURFACE OF AN ABSORBENT BODY

[75] Inventor: Yvon Levesque, Montreal, Canada
[73] Assignee: Johnson & Johnson Inc., Montreal, Canada
[21] Appl. No.: 996,476
[22] Filed: Dec. 31, 1992
[51] Int. Cl.⁵ ............................................. G01N 15/00
[52] U.S. Cl. .................................... 73/73; 73/64.51; 73/38
[58] Field of Search ........................ 73/73, 64.51, 38

[56] References Cited

U.S. PATENT DOCUMENTS

| | | | |
|---|---|---|---|
| 1,561,285 | 11/1925 | Sesler | 73/73 |
| 2,545,281 | 3/1951 | Hunt | 73/73 |
| 3,747,399 | 7/1973 | Treirat | 239/63 |
| 3,788,128 | 1/1974 | Strohecker | 73/73 |
| 3,884,067 | 5/1975 | Mottes | 73/73 |
| 3,952,584 | 4/1976 | Lichstein | 73/73 |
| 4,357,827 | 11/1982 | McConnell | 73/73 |
| 4,520,657 | 6/1985 | Marthaler | 73/73 |
| 4,581,921 | 4/1986 | Gillespie et al. | 73/73 |
| 4,976,138 | 12/1990 | Benninghoff et al. | 73/73 |
| 5,076,096 | 12/1991 | Blyler | 73/54.09 |
| 5,121,630 | 6/1992 | Clavin | 73/73 |

FOREIGN PATENT DOCUMENTS

| | | |
|---|---|---|
| 3200062 | 2/1987 | Japan . |
| 444330 | 3/1936 | United Kingdom . |
| 739385 | 6/1980 | U.S.S.R. . |
| 1406470 | 6/1988 | U.S.S.R. . |
| 1626141 | 2/1991 | U.S.S.R. . |

OTHER PUBLICATIONS

Soilmoisture Equipment Co., "Soilmoisture Probe", Sep. 1983, pp. 1–8.
F.A.L. Porous Media, "Fluid Transport on Porous Structure", Academic Press, 1992, p. 131.

*Primary Examiner*—Hezron E. Williams
*Assistant Examiner*—Joseph W. Roskos

[57] ABSTRACT

A method and apparatus for measuring the capillary attraction developed at a surface of an absorbent body intended to be used in a sanitary article such as a sanitary napkin, a diaper, a urinary pad, an adult brief, a tampon or a wound dressing, among others. The apparatus comprises a probe of fritted glass providing an array of capillary passageways in fluid communication with the interior of a closed cell completely filled with liquid. A pressure sensor mounted to the closed cell observes the liquid pressure therein. When the probe is placed in contact with the absorbent body, the capillary attraction exerted on liquid in the probe capillaries by the porous network of the absorbent body is transmitted through the liquid medium in the cell to the pressure sensor. The pressure data thus obtained reflects the state of dryness of the absorbent body surface. The capillary attraction measurement is made with no appreciable transfer of liquid toward the absorbent body to avoid altering its condition.

24 Claims, 2 Drawing Sheets

METHOD AND APPARATUS FOR THE MEASURING THE CAPILLARY ATTRACTION DEVELOPED AT A SURFACE OF AN ABSORBENT BODY

FIELD OF THE INVENTION

The present invention relates to a method and to a device for accurately measuring the intensity of the capillary attraction developed at a surface of an absorbent body intended to be used in a sanitary article, such as a sanitary napkin, a diaper, an adult brief, a urinary pad, a tampon or a wound dressing, among others. The invention is characterized by the ability to effect the capillary attraction measurement by a non-invasive procedure in order to avoid altering the moisture content of the absorbent body during the observation.

BACKGROUND OF THE INVENTION

In order to provide a complete understanding of the phenomena regulating the absorption of liquid in a disposable sanitary article, several instruments have been developed by the industry allowing to quantify various parameters of an absorbent system. Perhaps, the most basic of such instruments is the gravimetric absorbency test system (hereinafter "GATS") which is utilised to measure the ultimate absorbent capacity of a porous network. The GATS instrument comprises a horizontal porous plate made of fritted glass in fluid communication with a vertical burette filled with the appropriate test liquid, such as an aqueous solution. The test procedure consists of placing the sample material in contact with the fritted glass plate under constant pressure for allowing the sample material to absorb test liquid under the effect of capillary attraction. The test liquid is supplied at the interface between the fritted glass plate and the sample material under a negative pressure head of one centimeter which is achieved by maintaining the level of test liquid in the burette one centimeter below the top surface of the fritted glass plate. To prevent an undesirable pressure head increase due to the absorption of test liquid from the fritted glass plate an electromechanical control system replenishes the burette at the same rate as test liquid is withdrawn therefrom to maintain the level of test liquid constant.

The absorption of test liquid will cease when the residual capillary attraction of the sample material is counterbalanced by the negative pressure head. The amount of test liquid extracted from the burette is then observed and it is divided by the weight of the sample to obtain the maximal absorbent capacity of the sample material per unit of weight.

The GATS instrument is an extremely useful research tool because it allows to measure with high sensitivity and precision the maximal amount of body exudate that the absorbent system of a sanitary article can retain. Although this parameter is an important design factor during the development of absorbent systems capable to provide adequate protection against leakage and staining of the wearer's undergarment, one must also take in consideration the ability of the absorbent core to desorb the skin-contacting cover layer of the sanitary article which receives the fluid discharge. This is particularly important for absorbent articles such as sanitary napkins which are intended to be worn over a period of time during which several liquid discharges may occur. For such applications, the capability of the absorbent article to rapidly draw liquid away from the point of impact is critical in order to rapidly capture a liquid discharge and also to keep the cover layer of the sanitary article as dry as possible for maintaining the perineal region of the wearer free of moisture.

The GATS instrument does not have the ability of measuring the capillary attraction developed at a surface of a porous network because it functions by allowing a controlled liquid transfer toward the sample material, which necessarily alters the moisture contents at its surface. In contrast, the surface capillary attraction is a parameter which should be observed while no liquid is being delivered to the porous network.

In absence of any direct method for measuring the surface capillary attraction of an absorbent body, the industry has developed some indirect techniques which can which yield more meaningful results than the GATS instrument. All these techniques, however, rely to some degree on a controlled fluid transfer toward the absorbent body, which as discussed above introduces significant inaccuracies in the test results.

OBJECTS OF THE INVENTION

An object of the present invention is a method and a device for measuring the intensity of the capillary attraction developed at the surface of an absorbent body intended to be used in a sanitary article, such as a sanitary napkin, a diaper, an adult brief, a urinary pad, a tampon or a wound dressing, among others, without effecting a significant transfer of liquid thereto in order to prevent altering the condition of the absorbent body during the observation.

Further objects of the invention will become apparent from the following description.

SUMMARY OF THE INVENTION

As embodied and broadly described, the invention provides a device for measuring the intensity of the capillary attraction developed at a surface of an absorbent body (for the purpose of this specification "absorbent" shall solely mean the ability of a porous network to take-up liquid, irrespective of how liquid-retentive the porous network is. For example, the skin-contacting cover layer of sanitary article will be referred to as "absorbent body", although it is specifically designed to retain as little liquid as possible by transferring the liquid discharge to a reservoir layer underneath) for use in a sanitary article, said device comprising:

a substantially closed cell capable of holding a certain quantity of liquid, said cell having an outer probing surface for contacting the absorbent body, said probing surface being in liquid-communication with an interior of said cell through an array of capillary passageways; and a pressure sensor mounted to said cell for observing a pressure of liquid therein, whereby contact between said probing surface and the absorbent body gives rise to capillary attraction acting on liquid in said capillary passageways, calling a pressure variation in said cell which is observed by said pressure sensor, said substantially closed cell having the capability of restraining the liquid from freely egressing said capillary passageways under the influence of surface tension exerted by the absorbent body, thereby allowing to measure the intensity of the capillary attraction on the surface of the absorbent body without effecting any significant liquid transfer to the absorbent body.

The principal advantage of the measuring device in accordance with the invention resides in that it can perform the observation of the capillary attraction phenomenon without releasing any significant quantities of liquid to the absorbent body which would otherwise alter its condition. Accordingly, the measurement yields accurate data. This is achieved by providing a capillary continuum between the probing surface of the measuring device and the interior of the closed cell, having a bubbling pressure sufficiently high to prevent ingress of air through the capillary network under the effect of surface tension exerted on the liquid by the absorbent body.

In a preferred embodiment, a porous body such as a plate of fritted glass is utilized to provide the array of capillary passageways extending between the absorbent body and the liquid within the cell. The glass frit plate has a bubbling pressure in the range from about 50 millimeters of mercury (mmHg) to about 780 mmHg. Most preferably, the bubbling pressure is in the range from about 100 mmHg to about 500 mmHg.

The pressure sensor is preferably an electronic transducer converting applied pressure into electrical energy. The electric output signal which represents the magnitude of pressure in the cell can be used to drive an electronic display or a chart plotter for recording the evolution of pressure relative to time.

As embodied and broadly described herein, the invention also provides a method for measuring the intensity of the capillary attraction developed at a surface of an absorbent body for use in a sanitary article, said method comprising the steps of:

contacting said surface with a body of liquid to give rise to a capillary attraction between said body of liquid and said absorbent body;

confining said body of liquid to prevent any substantial quantity of liquid from ingressing said absorbent body under the influence of surface tension exerted on said body of liquid by said absorbent body; and measuring a pressure of said body of liquid which is indicative of the intensity of the capillary attraction developed between said body of liquid and said absorbent body.

As embodied and broadly described herein, the invention also provides a combination, comprising:

a sanitary article having a liquid-absorbing surface;

a device for measuring an intensity of a capillary attraction developed at said liquid-absorbing surface, said device including:

a) a substantially closed cell holding a certain quantity of liquid, said cell having an outer probing surface contacting said liquid-absorbing surface, said probing surface being in liquid-communication with an interior of said cell through an array of capillary passageways; and b) a pressure sensor mounted to said cell for observing a pressure of said liquid, whereby contact between said probing surface and said liquid-absorbing surface gives rise to a capillary attraction acting on said liquid, causing a pressure variation in said cell which is observed by said pressure sensor, said substantially closed cell having the capability of confining said liquid from freely egressing said probing surface under the influence of surface tension exerted on said liquid by liquid-absorbing surface, thereby allowing to measure the intensity of the capillary attraction on said liquid-absorbing surface without effecting any significant transfer of liquid thereto.

DESCRIPTION OF PREFERRED EMBODIMENTS

Figure 1:
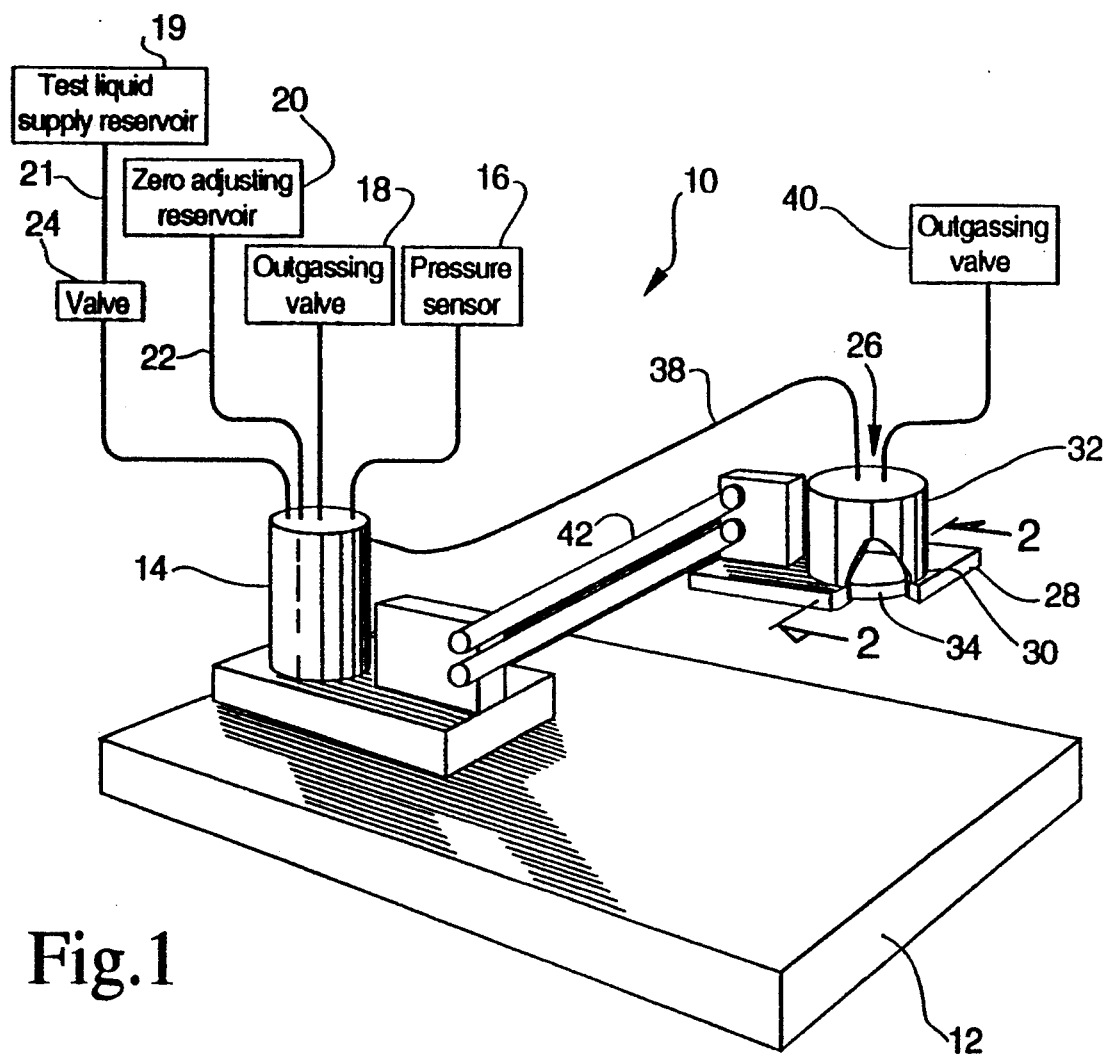
FIG. 1 is a perspective, schematical view of a device for measuring the intensity of the capillary attraction developed at the surface of an absorbent body, constructed in accordance with the present invention.

A schematical view of a measuring device, in accordance with the invention, is shown in FIG. 1. The measuring device, designated comprehensively by the reference numeral 10 comprises a supporting plate 12 to which is mounted a vertically extending generally cylindrical receptacle 14 made of transparent hard plastic material, such as an acrylic resin commercialized under the trade mark PLEXIGLASS. A pressure sensor 16 is mounted to the receptacle 14 to observe the magnitude of the pressure therein. Advantageously, the pressure sensor 16 is an electronic transducer generating an electric output signal proportional to the magnitude of the pressure in the receptacle 14. A pressure transducer available from the SENSOTEC INC. company, model V-2505-02 or model V-1945-2 rated at 105 mmHg and 780 mmHg, respectively, has been found satisfactory.

On the top wall of the receptacle 14 is mounted a manually operated outgassing valve 18 permitting to release air or other gases trapped in the receptacle 14.

A reservoir 19 is in fluid communication through a conduit 21 and through a manually operated valve 24 with the receptacle 14, for supplying test liquid thereto and to any other liquid containing chamber connected to the receptacle 14. During the normal use of the measuring device 10, the valve 24 is maintained closed to isolate the reservoir 19 from the receptacle 14. The valve 24 is opened only during the calibration and the preparation of the measuring device 10 for a test run, when desired for example to replenish the receptacle 14 with test liquid.

A small completely closed chamber 20 made of PLEXIGLASS (trademark) material is connected to the receptacle 14 through a flexible conduit 22 permitting to vertically displace the chamber 20 relative to the receptacle 14. By locating the chamber 20 at the selected vertical position, a pressure head, either positive or negative, of the desired magnitude, can be established in the receptacle 14 to compensate any over pressure or under pressure therein. In other words, the chamber 20 can be used as a simple zero adjuster for the pressure sensor 16.

To facilitate the vertical positioning of the chamber 20, a simple mechanical lifting device could be used, preferably manually operated, to precisely locate the chamber 20 at the desired elevation relative to the receptacle 14. Such elevating device has not been illustrated in the drawings since its construction and operation would be obvious to a man skilled in the art and furthermore it does not form part of the present invention.

Figure 2:
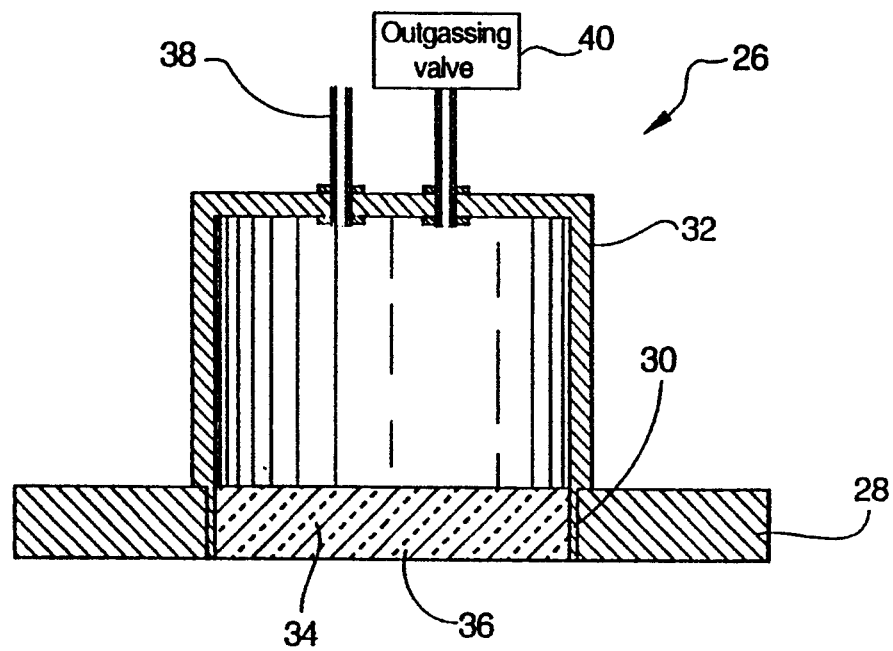
FIG. 2 is an enlarged cross-sectional view taken along lines 2—2 in FIG. 1.

The measuring device 10 also comprises a probe assembly 26, best shown in FIG. 2, including a plate 28 made of acrylic resin such as PLEXIGLASS (trademark) in which is drilled a vertically extending bore 30. In the bore 30 is press fitted an inverted cup-shaped housing 32 which carries a circular plate 34 made of fritted glass. The cup-shaped housing 32 completely encloses the plate 34 except its lower surface 36 which is flush with the lower surface of the plate 28 and constitutes the probing surface of the measuring device 10. To provide a fluid-tight seal between the walls of the housing 32 and the periphery of the fritted glass plate 34, a joint of epoxy adhesive is provided therein which also contributes to structurally unite the two components together.

The cup-shaped housing 32 is in fluid communication with the receptacle 14 through a flexible conduit 38. A manually operated outgassing valve 40 is mounted on the top surface of cup-shaped housing 32 to evacuate air trapped therein.

The fritted glass plate 34 defines a tri-dimensional array of capillary passageways establishing a multiplicity of fine fluid paths between the probing surface 36 and the interior of the cup-shaped housing 32. When the capillary network is completely filled with liquid air is prevented from entering therein even when the liquid is subjected to the influence of surface tension tending to suck liquid out from the exposed probing surface 36. Such surface tension occurs when the probing surface 36 contacts a porous network whose capillary attraction is to be measured. Stated otherwise, the liquid filling the capillary network of the fritted glass plate 34 forms a liquid barrier between the porous network and the interior of the cup-shaped housing 32, capable to act as a pressure transmissive medium, and also forming an air-tight seal preventing air from entering the cup-shaped housing which otherwise would allow liquid to leak out of the probing surface 36. The integrity of the air-tight seal can be maintained up to the point at which the pressure differential across the plate 34 overwhelms the surface tension at the boundary between the liquid and the glass grains of the plate 34, resulting into a rupture of the liquid films obturating the individual capillaries.

The magnitude of the pressure differential at which the air-tight seal established by a porous body is ruptured is known as the "bubbling pressure". This parameter is primarily dependent upon the pore size of the body; the finer the cross-sectional dimension of the pores, the higher the bubbling pressure will be. In practice, the bubbling pressure of a porous body is determined by performing a simple test which consists of completely saturating the pores of the body with liquid and then subjecting the porous body to an increasing pressure differential. The pressure at which the first bubbles appear on the surface of the porous body, indicating that the integrity of the air-tight seal is lost, constitutes the bubbling pressure value.

In the present case, a fritted glass plate having a bubbling pressure from about 50 mmHg to about 780 mmHg provides a broad working range for the measuring device 10. For pressure readings up to about 500 mmHg, a fritted glass plate available from the CAN-LAB company under catalog number 360-60-150 UF has been found satisfactory. For moderate pressures, up to 100 mmHg a fritted glass plate available from CAN-ADA WIDE SCIENTIFIC company under catalog number 4656-04 has been found satisfactory.

The pore size of the fritted glass plate 34 affects not only its bubbling pressure but also the rapidity at which a pressure wave can travel through liquid in the capillary network. This is an important characteristic which determines the response time of the measuring device 10. More particularly, a fritted glass plate having a fine pore size will transmit a pressure wave less rapidly than a fritted glass plate having larger capillaries. Accordingly, for a proper operation of the measuring device 10, the pore size of the fritted glass plate should be selected to yield a bubbling pressure sufficiently high for maintaining the integrity of the air-tight seal throughout the working range of the instrument, and also the bubbling pressure should be sufficiently low to provide an acceptable response time. For the fastest response time, the porosity should be such as to provide a bubbling pressure slightly in excess of the maximal pressure differential developed in response to the capillary attraction exerted by the porous network under observation.

As discussed above, the ability of the fritted glass plate 34 to resist releasing liquid under the influence of external capillary attraction is a critical aspect of the invention. To achieve this capability, in addition to an adequate bubbling pressure value, the liquid pressure transmissive mass between the fritted glass plate 34 and the pressure transducer 16 must be prevented from ingressing the capillaries of the fritted glass plate 34 through its surface exposed to the interior of the cup-shaped housing 32, otherwise liquid will be free to leave the probing surface 36. This is achieved by containing the liquid mass into a closed cell, constituted by the receptacle 14, the cup-shaped housing 32, the zero adjusting reservoir 20 and any associated tubing, which is entirely free of gas and is also structurally resistant to avoid any significant deformation under pressure tending to collapse the cell which occurs when the liquid at the probing surface 36 is subjected to capillary attraction. Since liquid is by nature an inexpansive medium, when it is contained into a rigid implosion-resistant cell, virtually no liquid will be allowed to leave the probing surface 36 until the pressure differential at which the liquid is exposed reaches the bubbling pressure of the fritted glass plate 34. At that moment, air enters in the cell through the capillaries of the plate 34, thereby allowing liquid to flow out of the probing surface 36.

Objectively, a very small quantity of liquid can escape the probing surface 36 primarily due to a minor deflection of the liquid containing cell under the applied pressure. As long as the liquid released does not substantially exceed 0.15 milliliters per square inch of the probing surface 36, the accuracy of the measuring device 10 is not significantly affected.

Referring back to FIG. 1, the probe assembly 26 is mounted to the support plate 12 by means of a parallelogram linkage 42 permitting to raise or lower the plate 28 while maintaining its bottom surface parallel with the support plate 12. The ability of the probe assembly 26 to move vertically is a desirable feature since it allows to adjust the position of the probing surface 36 in accordance with the thickness of the material under observation.

Figure 4:
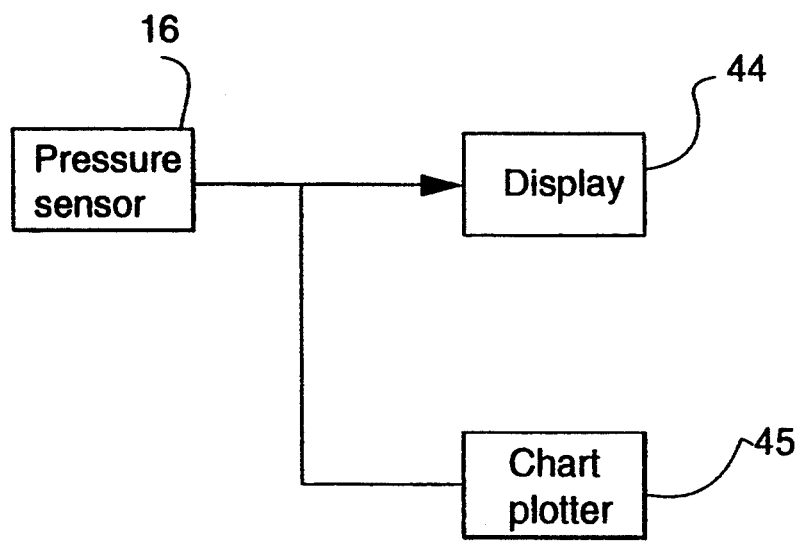
FIG. 4 is a schematical block diagram of the data displaying and recording system of the measuring device shown in FIG. 1.

With reference to FIG. 4, the pressure sensor 16, generating an electric output signal which represents the magnitude of pressure in the receptacle 14 can be used to drive an electronic display 44 to provide a readout of the instantaneous pressure in the receptacle 14. Also, the pressure sensor drives a chart plotter 45 recording the evolution of pressure relative to time. Such chart plotter can be a traditional plotter unit utilizing a movable stylus which marks a paper sheet or a computerized set-up storing the data for further processing at a later stage.

The operation of the measuring device 10 will be best understood from the following description of the test procedure for determining the capillary attraction developed at the surface of a sheeted absorbent.

Before using the measuring device 10, it must be prepared for the test run and calibrated in the following manner. The first step consists of completely degassing the liquid containing cell formed by the receptacle 14, the zero adjusting reservoir 20, the cup-shaped housing 32, the conduits 22 and 38, as well as the capillary void volume of the fritted glass plate 34. This is achieved by opening the outgassing valves 18 and 40 while discharging the test liquid in the receptacle 14 from the reservoir 19 through the valve 24. Liquid delivered in the receptacle 14 flows in the zero adjusting reservoir through the conduit 22 and in the cup-shaped housing through the conduit 38 where it fills the pores of the fritted glass plate 34. As the level of liquid in the liquid containing cell rises, air is expelled outside through the outgassing valves 18 and 40.

When the liquid containing cell is completely filled the flow of liquid is interrupted by closing the valve 24. To completely eliminate all trapped air bubbles, a vacuum pump is successively connected to the outgassing valves 18 and 40 to suck out occluded air. This operation is important allowing to dislodge fine air bubbles that would otherwise remain in the pores of the fritted glass plate 34, rendering the measuring device 10 inaccurate.

Once the measuring device 10 has been fully degassed, the outgassing valves 18 and 40 are closed and the pressure transducer 14 is calibrated by vertically displacing the reservoir 20 until the display 44 reads zero. The test procedure is then commenced by locating between the plate 28 and the supporting plate 12 the absorbent body whose surface capillary attraction is to be measured. When a physical contact between the probing surface 36 and the absorbent body is established, liquid in the fritted glass plate 34 is subjected to surface tension, exerted by the porous network of the absorbent body, tending to pull the liquid out of the fritted glass plate 34. By properly selecting the pore size of the fritted glass plate 34 whereby it can resist the ingress of air at the capillary attraction level developed by the absorbent body, and due to the inexpensive nature of the test liquid restrained in a rigid, closed cell, no significant amount of liquid is allowed to escape from the probing surface 36. However, the capillary attraction is transmitted through the body of liquid to the pressure sensor 16 and registers on the display 44, while the plotter 45 records the evolution of the capillary attraction relative to time.

To determine the maximal capillary attraction developed at the surface of the absorbent body, the probe assembly 26 is maintained in contact with the sample until no substantial pressure decrease is noted. As previously discussed, the response time of the measuring device 10 primarily depends upon the pore size of the fritted glass plate 34, for that reason, it is preferable to use a unit having a bubbling pressure marginally exceeding the pressure differential value generated in response to the maximal capillary attraction that the absorbent body can develop.

The measuring device 10 can be used to assess the capillary attraction when the absorbent body is dry or after it has absorbed a finite liquid discharge, in which case the measuring device 10 actually measures the residual capillary attraction at the surface of the absorbent body after an initial loading. The resulting data can be used for designing a sanitary article, such as a sanitary napkin, optimized to remain as dry as possible even after the occurrence of several fluid discharges.

The measuring device 10 can also be used for assessing the capillary attraction on an absorbent body under pressure, to simulate a situation where the wearer is sitting or exerts a pressure on the sanitary article. This is achieved by placing a weight on the plate 28 to establish the desired pressure on the sample.

The test liquid which can be used in the measuring device 10 can vary in accordance with the intended application. Liquids of aqueous nature have been found satisfactory, such as a solution of water containing 1% NaCl or real or synthetic menstrual liquid or real or synthetic urine.

The data obtained with the measurement device 10 is representative of the intensity of the capillary forces tending to draw liquid within the absorbent body under observation. Consequently, when the absorbent body is used as a cover layer of a sanitary article, the intensity of the surface capillary attraction provides a measure of the degree of dryness of the liquid-receiving surface after one or more liquid discharges. For applications in which the absorbent body is a reservoir layer in a compound absorbent system, the surface capillary attraction data allows to quantify the ability of the absorbent body to desorb the transfer layer which receives the liquid discharge. Accordingly, the measuring device 10 can be used to analyze individually the various components of a multi-layered absorbent system to provide a better understanding of each component behaviour which, in turn, allows to optimize the entire system for an enhanced liquid-absorptive performance.

Figure 3:
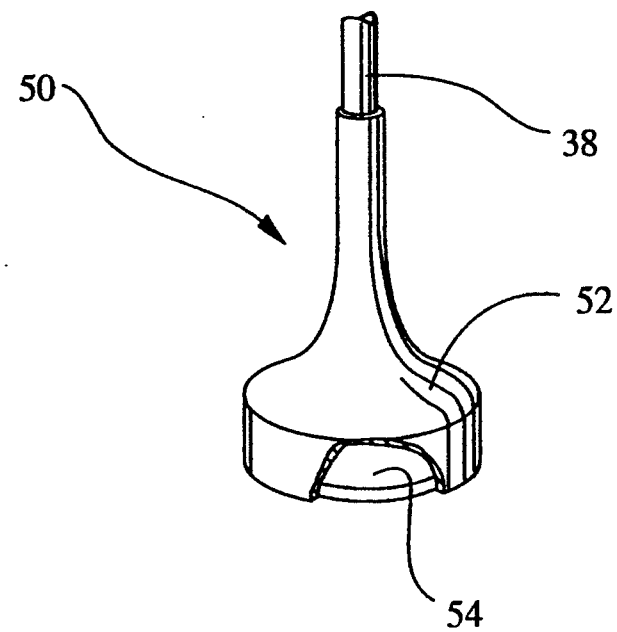
FIG. 3 is a schematical view of a probe assembly constructed in accordance with a variant.

FIG. 3 illustrates a variant of the probe assembly of the measuring device 10, designated by the numeral 50. The probe assembly 50, which is significantly smaller than the probe assembly 26, includes an inverted funnel-shaped housing 52 which carries a comparatively small fritted glass plate 54. The upper end of the funnel-shaped housing 52 connects with the tube 38. The probe assembly 50 forms a hand-held unit permitting to measure the capillary attraction at various locations on the surface of the absorbent body, allowing to establish a surface moisture distribution profile.

The scope of the present invention is not limited by the description, examples and suggestive uses herein, as modifications can be made without departing from the spirit of the invention. Thus, it is intended that the present application covers the modifications and variations of this invention provided that they come within the scope of the appended claims and their equivalents.

We claim:

1. A device for measuring the intensity of the capillary attraction developed at a surface of an absorbent body for use in a sanitary article, said device comprising:

a substantially closed cell capable of holding a certain quantity of liquid, said cell having an outer probing surface for contacting the absorbent body, said probing surface being in liquid-communication with an interior of said cell through an array of capillary passageways; and a pressure sensor mounted to said cell for observing a pressure of liquid in said cell, whereby contact between said probing surface and the absorbent body gives rise to a capillary attraction acting on liquid in said array of capillary passageways, causing a pressure variation in said cell which is observed by said pressure sensor, said substantially closed cell having the capability of restraining liquid from freely egressing said probing surface under the influence of surface tension exerted thereon by the absorbent body, thereby allowing to measure the intensity of the capillary attraction on the surface of the absorbent body without effecting any significant transfer of liquid thereto.

2. A device as defined in claim 1, comprising a porous body forming said array of capillary passageways, an outer surface of said porous body constituting said probing surface.

3. A device as defined in claim 2, wherein said probing surface is generally planar.

4. A device as defined in claim 2, wherein said porous body is mounted in a housing, said housing enclosing said porous body on all sides except said probing surface.

5. A device as defined in claim 4, wherein said housing is mounted to a flexible conduit establishing a liquid path between said porous body and said pressure sensor, said flexible conduit permitting to move said porous body relative to said pressure sensor.

6. A device as defined in claim 2, wherein said porous body comprises a fritted glass plate.

7. A device as defined in claim 1, wherein said array of capillary passageways has a bubbling pressure in the range from about 50 mmHg to about 780 mmHg.

8. A device as defined in claim 1, wherein said array of capillary passageways has a bubbling pressure in the range from about 100 mmHg to about 500 mmHg.

9. A device as defined in claim 1, wherein said pressure sensor includes an electronic transducer generating an electric output signal representative of the pressure of liquid in said cell.

10. A device as defined in claim 9, further comprising an electronic display responsive to said electronic transducer for indicating an instantaneous pressure of liquid in said cell.

11. A device as defined in claim 9, further comprising a system responsive to said electronic transducer for recording an evolution of the pressure of liquid in said cell relative to time.

12. A device as defined in claim 1, wherein said cell is substantially rigid to prevent collapse thereof due to negative pressure generated therein in response to capillary attraction exerted on liquid in said cell by the absorbent body.

13. A device as defined in claim 1, wherein said cell includes an outgassing valve for releasing air trapped in said cell.

14. A method for measuring the intensity of the capillary attraction developed at a surface of an absorbent body for use in a sanitary article, said method comprising the steps of:

contacting said surface with a body of liquid to give rise to a capillary attraction between said body of liquid and said absorbent body;

restraining said body of liquid from freely ingressing said absorbent body under the influence of surface tension exerted on said body of liquid by said absorbent body; and measuring a pressure in said body of liquid which is indicative of the capillary attraction developed between said body of liquid and said absorbent body.

15. A method as defined in claim 14, comprising the step of maintaining said body of liquid in contact with said surface until said pressure substantially stabilizes.

16. A method as defined in claim 14, comprising the step of recording an evolution of said pressure relative to time.

17. A method as defined in claim 14, further comprising the step of:

delivering to said absorbent body a finite amount of liquid which is absorbed therein;

applying said body of liquid to said surface to measure the intensity of a residual capillary attraction developed by said absorbent body.

18. A method as defined in claim 14, comprising the step of compressing said absorbent body while measuring the intensity of the capillary attraction developed at said surface.

19. A method as defined in claim 14, wherein said sanitary article is selected from the group consisting of a sanitary napkin, a diaper, a urinary pad, an adult brief, a tampon and a wound dressing.

20. A method as defined in claim 14, comprising:

confining said body of liquid in a substantially closed cell comprising a probing surface which is in liquid-communicative relationship with an interior of said cell through an array of capillary passageways;

contacting said absorbent body with said probing surface; and measuring a pressure in said cell to determine the intensity of the capillary attraction developed at the surface of said absorbent body.

21. In combination:

a sanitary article having a liquid-absorbing surface;

a device for measuring an intensity of a capillary attraction developed at said liquid-absorbing surface, said device including:

a) a substantially closed cell holding a certain quantity of liquid, said cell having an outer probing surface contacting said liquid-absorbing surface, said probing surface being in liquid-communication with an interior of said cell through an array of capillary passageways; and b) a pressure sensor mounted to said cell for observing a pressure of said liquid, whereby contact between said probing surface and said liquid-absorbing surface gives rise to a capillary attraction acting on said liquid, causing a pressure variation in said cell which is observed by said pressure sensor, said substantially closed cell having the capability of restraining said liquid from freely egressing said probing surface under the influence of surface tension exerted thereon by the absorbent body, thereby allowing to measure the intensity of the capillary attraction on the surface of the absorbent body without effecting any significant transfer of liquid thereto.

22. A combination as defined in claim 21, wherein said probing surface is relatively planar.

23. A combination as defined in claim 21, wherein said array of capillary passageways has a bubbling pressure in the range from about 50 mmHg to about 780 mmHg.

24. A combination as defined in claim 21, wherein said array of capillary passageways has a bubbling pressure in the range from about 100 mmHg to about 500 mmHg.

* * * * *